United States Patent [19]  [11] 4,433,149
Lee  [45] Feb. 21, 1984

[54] ESTERS OF UREIDO-PHENYL (OR PYRIDYL) PHOSPHINIC ACIDS

[75] Inventor: Shy-Fuh Lee, Sunnyvale, Calif.

[73] Assignee: Zoecon Corporation, Palo Alto, Calif.

[21] Appl. No.: 379,584

[22] Filed: May 19, 1982

Related U.S. Application Data

[63] Continuation-in-part of Ser. No. 296,031, Aug. 25, 1981, abandoned.

[51] Int. Cl.[3] ............................ C07F 9/32; C07F 9/58
[52] U.S. Cl. ...................................... 546/21; 546/22; 546/24; 260/938
[58] Field of Search ............................ 546/21, 22, 24; 260/938

[56] References Cited
PUBLICATIONS

Somasekhara et al., Current Science, No. 18: 529–530, (1968).

Primary Examiner—Richard Raymond
Assistant Examiner—Bernard Dentz
Attorney, Agent, or Firm—Jacqueline S. Larson; Donald W. Erickson

[57] ABSTRACT

Substituted tetrahydrobenzodiazaphosphorindiones or tetrahydropyridodiazaphosphorindiones, intermediates therefore, synthesis thereof, said compounds being useful herbicides.

5 Claims, No Drawings

ESTERS OF UREIDO-PHENYL (OR PYRIDYL) PHOSPHINIC ACIDS

This is a continuation-in-part of Ser. No. 296,031, filed on Aug. 25, 1981, now abandoned, the entire disclosure of which is incorporated herein by reference.

This invention relates to novel substituted tetrahydrobenzodiazaphosphorindiones, tetrahydropyridodiazaphosphorindiones, intermediates therefor, synthesis thereof, said compounds being useful herbicides.

The compounds of the present invention are represented by the following formula (A):

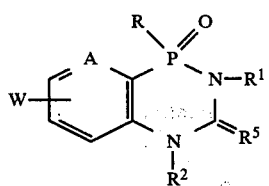

(A)

wherein,

A is CH or N;

R is lower alkyl or phenyl;

$R^1$ is hydrogen, lower alkyl, lower cycloalkyl, phenyl or substituted phenyl;

$R^2$ is hydrogen, lower alkyl, lower haloalkyl, lower cyanoalkyl, or lower alkoxyalkyl;

$R^5$ is oxygen or sulfur; &

W is hydrogen, lower alkyl, lower haloalkyl, lower alkoxy, lower alkylthio, lower alkylsulfinyl, lower alkylsulfonyl, halogen or the group

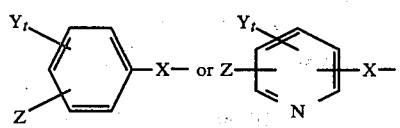

where X is oxygen, sulfur, sulfinyl or sulfonyl; t is zero, one or two; and each of Y and Z is independently hydrogen, lower alkyl, lower alkoxy, lower haloalkyl, lower haloalkoxy, or halogen.

The compounds of formula (A) are effective herbicidal agents against grasses and broad-leaved plants.

Synthesis of the compounds of the present invention (where $R^2$=H) may be outlined as follows ($R^3$=lower alkyl):

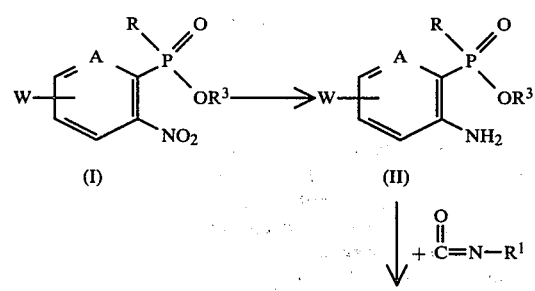

In the above synthesis, the nitrophenylphosphinate or nitropyridylphosphinate (I) is hydrogenated to the aminophenylphosphinate or aminopyridylphosphinate (II). The phosphinate (II) is then reacted with an N-substituted isocyanate in an organic solvent such as toluene or chlorobenzene and with or without a base such as triethylamine to give the phosphinophenyl- or phosphinopyridylurea (III). The urea is then cyclized by treating with, for example, phosgene or concentrated sulfuric acid or sodium methoxide in a solvent such as toluene or methanol and with heating under reflux to give a compound of the present invention of formula (A').

Alternatively, the compounds of the present invention (where $R^2$=H) may be prepared as follows:

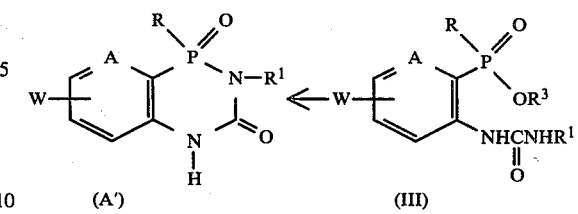

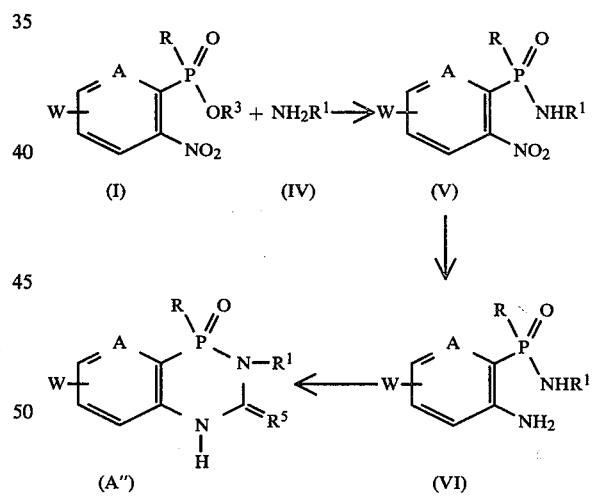

In the above synthesis, the nitrophenyl- or nitropyridylphosphinate (I) is treated with phosgene, thionylchloride or oxalyl chloride and then is reacted with an amine (IV) to give the phosphinamide (V). The phosphinamide (V) is hydrogenated to the aminophenyl- or amino-pyridylphosphinamide (VI), which is cyclized with phosgene or thiophosgene in a solvent such as chlorobenzene or toluene to give a compound of the present invention of formula (A'').

A third method of synthesis is outlined below:

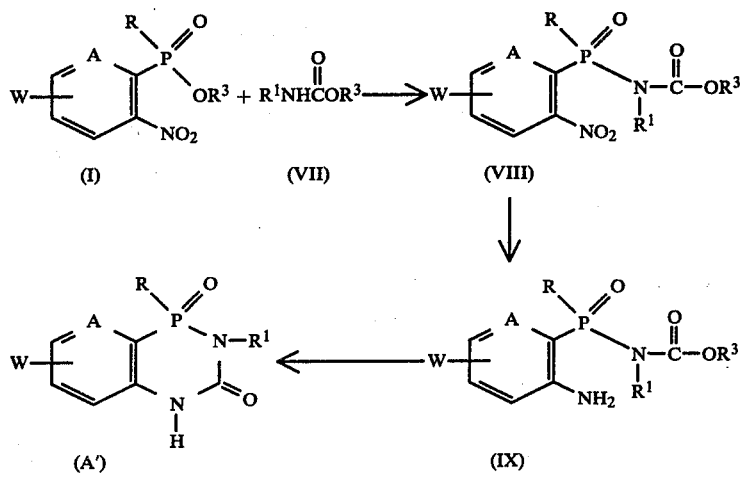

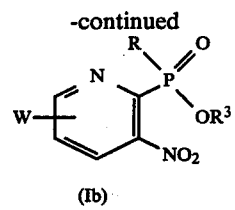

In the above synthesis, the nitrophenyl- or nitropyridylphosphinate (I) is treated with phosgene, thionyl chloride or oxalyl chloride & then is reacted with a carbamate (VII) to give a N-carboxyphosphinamide (VIII). The compound (VIII) is hydrogenated to the corresponding amino compound (IX), which is cyclized as previously described to give a compound of the present invention of formula (A').

Synthesis of the compounds of formula (I) where A=CH may be outlined as follows:

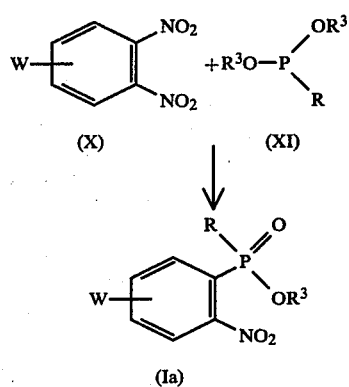

In the above synthesis, the dinitrobenzene (X) is phosphinylated with the phosphonite (XI) at room temperature or at refluxing temperature to give the corresponding phosphinate (Ia), following the procedure outlined by Cadogan et al., *J. Chem. Soc.* (C): 1314 (1969). The reaction may be carried out neat or in the presence of a solvent such as acetonitrile or tetrahydrofuran or toluene.

Synthesis of the compounds of formula (I) where A=N may be outlined as follows:

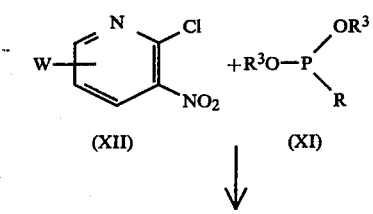

-continued

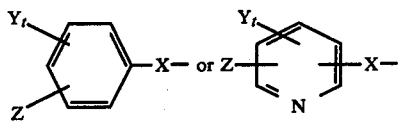

In the above synthesis, the 3-nitropyridine (XIII) is phosphinylated by reaction with the phosphonite (XI) in the presence of a metal catalyst such as nickel chloride at an elevated temperature and under a nitrogen atmosphere to give the phosphinate (Ib).

Compounds of formula I where W is lower alkoxy, lower alkylthio, or the group

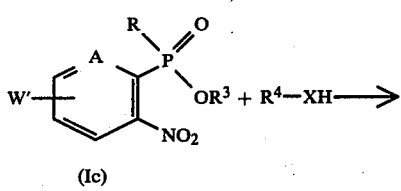

may be prepared as follows (W'=Cl or Br; R⁴=lower alkyl, phenyl or pyridyl):

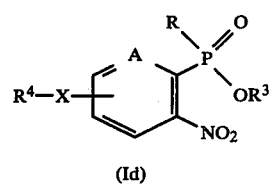

In the above synthesis, the phosphinate (Ic) and an alcohol $R^4$-OH or a thiol $R^4$-SH are reacted together in the presence of a base such as potassium hydroxide or potassium carbonate with or without a solvent such as ethanol or dimethylformamide at an elevated temperature. Alternatively, the phosphinate (Ic) and $R^4$—OH or R⁴SH in a solvent such as ethanol or dimethylsulfoxide are reacted with aqueous sodium hydroxide to give the phosphinic acid (XIII), which is then

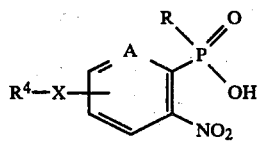
XIII reacted with, for example, diazomethane in methanol, or methyl or ethyl iodide in acetone with a base such as potassium carbonate.

To prepare compounds of formula (A) where W is lower alkylsulfinyl, lower phenylsulfinyl or lower pyridylsulfinyl, a compound of formula (A) where W=lower alkylthio, lower phenylthio or lower pyridylthio is reacted with sodium periodate in an organic solvent such as methanol and at a temperature below room temperature, most usually at about 0° C.

To prepare compounds of formula (A) where W is lower alkylsulfonyl, lower phenylsulfonyl or lower pyridylsulfonyl, a compound of formula (A) where W=lower alkylthio, lower phenylthio or lower pyridylthio in a solvent such as acetic acid is reacted with hydrogen peroxide at room temperature.

Compounds of formula (A) where $R^2$ is other than hydrogen are prepared after cyclization is completed by alkylation of a compound of formula (A') or (A").

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "lower alkylthio" refers to an alkylthio group, straight or branched, having a chain length of one to eight carbon atoms.

The term "lower alkylsulfinyl" refers to an alkylsulfinyl group, straight or branched, of one to eight carbon atoms.

The term "lower alkylsulfonyl" refers to an alkylsulfonyl group, straight or branched, of one to eight carbon atoms.

The term "lower cycloalkyl" refers to a cycloalkyl group of three to eight cyclic carbon atoms.

The term "substituted phenyl" refers to a phenyl group substituted at one, two or three of the ring carbon atoms by radicals selected from halogen, lower alkyl, lower alkoxy, lower haloalkyl, or lower alkylthio.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half to ten pounds per acre.

Methods of preparing herbicidal formulations which can be used with a compound of the present invention are known in the art. In the preparation of the herbicidal compositions, a compound of the present invention can be uniformly mixed with or dissolved in suitable adjuvants such as a solid carrier, for example talc, clay, kaolin, diatomaceous earth or silica gel; a liquid carrier, for example alcohols, dioxane, acetone, methyl naphthalene or dimethylformamide; surfactants as emulsifiers, dispersing agents or wetting agents, for example alkyl sulfate, alkyl sulfonate, polyoxyethyleneglycol ethers or polyoxyethylenealkylaryl ethers; and carboxymethyl cellulose, gum arabic and other adjuvants.

The compounds of the present invention are effective on broad-leaf weeds and the grassy weeds or graminaceous weeds. The optimum usage of a compound of the present invention is readily determinable by one of ordinary skill in the art using routine testing such as greenhouse testing and small plot testing.

The compounds of the present invention also are useful as fungicides for the control of pathogenic diseases of plants.

The following examples are provided to illustrate the practice of the present invention. Temperature is given in degrees Centigrade. "RT" means room temperature.

EXAMPLE 1

A mixture of 1,2-dinitrobenzene (2.48 mmol), diethyl methylphosphonite (3.72 mmol) and acetonitrile (3 ml) is stirred at RT overnight. The reaction is concentrated to dryness, and the residue is purified by preparative thin layer chromatography (TLC) to yield ethyl P-methyl-2-nitrophenyl-phosphinate.

A solution of ethyl P-methyl-2-nitrophenylphosphinate (10 mmol) in ethanol (40 ml) containing 10% palladium on carbon (200 mg) is hydrogenated at atmospheric pressure. After cessation of hydrogen uptake, the mixture is filtered and evaporated to dryness to give ethyl P-methyl-2-aminophenylphosphinate.

To a solution of ethyl P-methyl-2-aminophenylphosphinate (22.8 mmol) in toluene (50 ml) containing triethylamine (22.8 mmol) is added, at 0°, a solution of N-isopropylisocyanate (27.4 mmol) in toluene (20 ml). The mixture is stirred at RT for two hours and is then washed with brine, dried and evaporated to obtain N-[2-(ethyl P-methylphosphino)phenyl]-N'-isopropylurea.

A solution of N-[2-(ethyl P-methylphosphino)-phenyl]-N'-isopropylurea (2.0 g) in toluene (20 ml) containing phosgene (4 equiv.) is heated under reflux for six hours. Excess phosgene and toluene are removed by distillation to yield 1-methyl-2-isopropyl-4H-1,2,3,4-tetrahydro-2,4,1-benzodiazaphosphorin-1,3-dione.

Alternatively, the above urea (2.0 g) is treated with 30% sodium methoxide (2 equiv.) in methanol (20 ml). The mixture is heated under reflux for eight hours, after which it is concentrated to a small volume and poured into water. The equeous solution is acidified with HCl and filtered. The solid is dried to obtain 1-methyl-2-isopropyl-4H-1,2,3,4-tetrahydro-2,4,1-benzodiazaphosphorin-1,3-dione.

As a third method, a solution of the above urea (1.2 g) in toluene (25 ml) containing concentrated sulfuric acid (5 drops) is heated under reflux for 24 hours. It is then concentrated and taken up in methylene chloride. The methylene chloride solution is washed with water, dried and evaporated to give 1-methyl-2-isopropyl-4H-1,2,3,4-tetrahydro-2,4,1-benzodiazaphosphorin-1,3,dione.

EXAMPLE 2

A mixture of 4-chloro-1,2-dinitrobenzene (3.31 mmol) and diethyl methylphosphonite (5.30 mmol) in 3 ml of acetonitrile is stirred at RT overnight. The mixture is then concentrated and the residue is purified by preparative TLC to yield ethyl P-methyl-2-nitro-5-chlorophenylphosphinate.

Following the above procedure or that of Example 1, each of 4-methoxy-1,2-dinitrobenzene; 4-ethyl-1,2-dinitrobenzene; 4-bromo-1,2-dinitrobenzene; 3,4-dinitrotoluene and trifluoro-3,4-dinitrotoluene is reacted with diethyl methylphosphonite to give, respectively,
ethyl P-methyl-2-nitro-5-methoxyphenylphosphinate,
ethyl P-methyl-2-nitro-5-ethylphenylphosphinate,
ethyl P-methyl-2-nitro-5-bromophenylphosphinate,
ethyl P-methyl-2-nitro-5-methylphenylphosphinate,
ethyl P-methyl-2-nitro-5-trifluoromethylphenylphosphinate, and
ethyl P-methyl-2-nitro-5-isopropylphenylphosphinate.

Each of the above seven nitrophenylphosphinates is hydrogenated following the procedure of Example 1 to obtain the corresponding aminophenylphosphinates, which are then each reacted with N-isopropylisocyanate to give, respectively,
N-[2-(ethyl P-methylphosphino)-4-chlorophenyl]-N'-isopropylurea,
N-[2-(ethyl P-methylphosphino)-4-methoxyphenyl]-N'-isopropylurea,
N-[2-(ethyl P-methylphosphino)-4-ethylphenyl]-N'-isopropylurea,
N-[2-(ethyl P-methylphosphino)-4-bromophenyl]-N'-isopropylurea,
N-[2-(ethyl P-methylphosphino)-4-methylphenyl]-N'-isopropylurea,
N-[2-(ethyl P-methylphosphino)-4-trifluoromethylphenyl]-N'-isopropylurea, and
N-[2-(ethyl P-methylphosphino)-4-isopropylphenyl]-N'-isopropylurea.

Following the procedure of Example 1, each of the above ureas is cyclized to yield, respectively,
7-chloro-1-methyl-2-isopropyl-4H-1,2,3,4-tetrahydro-2,4,1-benzodiazaphosphorin-1,3-dione;
7-methoxy-1-methyl-2-isopropyl-4H-1,2,3,4-tetrahydro-2,4,1-benzodiazaphosphorin-1,3-dione;
7-ethyl-1-methyl-2-isopropyl-4H-1,2,3,4-tetrahydro-2,4,1-benzodiazaphosphorin-1,3-dione;
7-bromo-1-methyl-2-isopropyl-4H-1,2,3,4-tetrahydro-2,4,1-benzodiazaphosphorin-1,3-dione;
1,7-dimethyl-2-isopropyl-4H-1,2,3,4-tetrahydro-2,4,1-benzodiazaphosphorin-1,3-dione;
1-methyl-2-isopropyl-7-trifluoromethyl-4H-1,2,3,4-tetrahydro-2,4,1-benzodiazaphosphorin-1,3-dione; and
1-methyl-2,7-diisopropyl-4H-1,2,3,4-tetrahydro-2,4,1-benzodiazaphosphorin-1,3-dione.

EXAMPLE 3

Following the procedure of Example 1, ethyl P-methyl-2-aminophenylphosphinate is reacted with each of phenylisocyanate, methylisocyanate, cyclohexylisocyanate and (4-chlorophenyl)-isocyanate to yield, respectively,
N-[2-(ethyl P-methylphosphino)phenyl]-N'-phenylurea,
N-[2-(ethyl P-methylphosphino)phenyl]-N'-methylurea,
N-[2-(ethyl P-methylphosphino)phenyl]-N'-cyclohexylurea, and
N-[2-(ethyl P-methylphosphino)phenyl]-N'-(4-chlorophenyl)urea.

Each of the above ureas is cyclized to yield, respectively,
1-methyl-2-phenyl-4H-1,2,3,4-tetrahydro-2,4,1-benzodiazaphosphorin-1,3-dione;
1,2-dimethyl-4H-1,2,3,4-tetrahydro-2,4,1-benzodiazaphosphorin-1,3-dione;
1-methyl-2-cyclohexyl-4H-1,2,3,4-tetrahydro-2,4,1-benzodiaza phosphorin-1,3-dione; and
1-methyl-2-(4-chlorophenyl)-4H-1,2,3,4-tetrahydro-2,4,1-benzodiazaphosphorin-1,3-dione.

EXAMPLE 4

To a solution of ethyl P-methyl-2-nitro-5-chlorophenylphosphinate (20.0 mmol) and ethanethiol (60.0 mmol) in dimethylsulfoxide (20 ml) is added a solution of sodium hydroxide (40.0 mmol) in 1 ml of water. The mixture is warmed to 60° overnight, after which it is poured into water and extracted with ether. The aqueous solution is acidified, extracted with methylene chloride, dried and evaporated to give P-methyl-2-nitro-5-ethylthiophenylphosphinic acid, which is then treated with diazomethane in methanol to give methyl P-methyl-2-nitro-5-ethylthiophenylphosphinate.

To a solution of methyl P-methyl-2-nitro-5-ethylthiophenylphosphinate (3.6 g) in 5% aqueous acetic acid (40 ml) is added 3.0 g of iron by portions at reflux temperature. After addition is complete, the mixture is heated under reflux for another 2 hours. The reaction mixture is filtered and the filtrate is extracted with methylene chloride (3X). The combined extracts are washed, dried and concentrated to dryness to yield methyl P-methyl-2-amino-5-ethylthiophenylphosphinate.

The above aminophenylphosphinate is reacted with N-isopropylisocyanate, following the procedure of Example 1 to give N-[2-(methyl P-methylphosphino)-4-ethylthiophenyl]-N'-isopropylurea, which is then cyclized to give 7-ethylthio-1-methyl-2-isopropyl-4H-1,2,3,4-tetrahydro-2,4,1-benzodiazaphosphorin-1,3-dione.

EXAMPLE 5

To a solution of 7-ethylthio-1-methyl-2-isopropyl-4H-1,2,3,4-tetrahydro-2,4,1-benzodiazaphosphorin-1,3-dione (50.0 mmol) in 20 ml of methanol is added, at 0°, a solution of sodium periodate (66.0 mmol) in 4 ml of water. After reaction is completed, the reaction mixture is concentrated to a small volume at lower temperature. The resulting slurry is poured into water and extracted with methylene chloride. The extract is washed with brine, dried and evaporated to yield 7-ethylsulfinyl-1-methyl-2-isopropyl-4H-1,2,3,4-tetrahydro-2,4,1-benzodiazaphosphorin-1,3,-dione.

EXAMPLE 6

To a solution of 7-ethylthio-1-methyl-2-isopropyl-4H-1,2,3,4-tetrahydro-2,4,1-benzodiazaphosphorin-1,3-dione (50.0 mmol) in 10 ml of acetic acid is added dropwise, at RT, 30% hydrogen peroxide (500.0 mmol). After reaction is completed, the reaction mixture is diluted with water and extracted with methylene chloride. The extract is washed with brine, dried and evaporated to give 7-ethylsulfonyl-1-methyl-2-isopropyl-4H-1,2,3,4-tetrahydro-2,4,1-benzodiazaphosphorin-1,3-dione.

EXAMPLE 7

Following the procedure of Example 1, each of 4-phenoxy-1,2-dinitrobenzene, 4-(4-chlorophenoxy)-1,2-dinitrobenzene and 4-(2-chloro-4-trifluoromethylphenoxy)-1,2-dinitrobenzene is reacted with diethyl methylphosphonite to give, respectively,
ethyl P-methyl-2-nitro-5-phenoxyphenylphosphinate,
ethyl P-methyl-2-nitro-5-(4-chlorophenoxy)phenylphosphinate, and
ethyl P-methyl-2-nitro-5-(2-chloro-4-trifluoromethylphenoxy)phenylphosphinate.

Each of the above nitrophenylphosphinates is hydrogenated to the corresponding aminophenylphosphinate, which is then reacted with N-isopropylurea to obtain, respectively,
N-[2-(ethyl P-methylphosphino)-4-phenoxyphenyl]-N'-isopropylurea,
N-[2-(ethyl P-methylphosphino)-4-(4-chlorophenoxy)phenyl]-N'-isopropylurea, and
N-[2-(ethyl P-methylphosphino)-4-(2-chloro-4-trifluoromethylphenoxy)phenyl]-N'-isopropylurea.

Each of the above ureas is cyclized to yield, respectively,
7-phenoxy-1-methyl-2-isopropyl-4H-1,2,3,4-tetrahydro-2,4,1-benzodiazaphosphorin-1,3-dione;
7-(4-chlorophenoxy)-1-methyl-2-isopropyl-4H-1,2,3,4-tetrahydro-2,4,1-benzodiazaphosphorin-1,3-dione; and
7-(2-chloro-4-trifluoromethylphenoxy)-1-methyl-2-isopropyl-4H-1,2,3,4-tetrahydro-2,4,1-benzodiazaphosphorin-1,3-dione.

EXAMPLE 8

To a mixture of ethyl P-methyl-2-nitro-5-chlorophenylphosphinate (20.0 mmol) and thiophenol (40.0 mmol) in 20 ml of ethanol is added sodium hydroxide (60.0 mmol) in 1 ml of water. The mixture is heated under reflux for 24 hours. The reaction mixture is poured into water, acidified with dilute HCl and extracted with methylene chloride (2X). The combined extracts are washed with brine, dried and evaporated to dryness. The resulting oily residue is treated with diazomethane in methanol, concentrated and purified by preparative TLC to yield methyl P-methyl-2-nitro-5-phenylthiophenylphosphinate.

To a mixture of methyl P-methyl-2-nitro-5-phenylthiophenylphosphinate (3.0 g) and ammonium chloride (5.3 g) in 40 ml of ethanol and 20 ml of water is heated to 70°, and iron (3.0 g) is added portionwise over a period of about 10 minutes. After the reaction is completed, the reaction mixture is filtered and the filtrate is concentrated to a small volume, followed by extraction with methylene chloride, drying and evaporation to give methyl P-methyl-2-amino-5-phenylthiophenylphosphinate.

Following the procedures of Example 1, the above aminophenylphosphinate is reacted with N-isopropylisocyanate to give N-[2-(methyl P-methylphosphino)-4-phenylthiophenyl]-N'-isopropylurea, which is then cyclized to yield 7-phenylthio-1-methyl-2-isopropyl-4H-1,2,3,4-tetrahydro-2,4,1-benzodiazaphosphorin-1,3-dione.

In like manner, 7-(4-chlorophenylthio)-1-methyl-2-isopropyl-4H-1,2,3,4-tetrahydro-2,4,1-benzodiazaphosphorin-1,3-dione is prepared from ethyl P-methyl-2-nitro-5-chlorophenylphosphinate and 4-chlorophenylthiol.

EXAMPLE 9

Following the procedure of Example 1, ethyl P-ethyl-2-aminophenylphosphinate is prepared from 1,2-dinitrobenzene and diethyl ethylphosphonite, followed by hydrogenation. It is then reacted with N-isopropylisocyanate to give N-[2-(ethyl P-ethylphosphino)phenyl]-N'-isopropylurea.

In the same manner, N-[2-(ethyl P-ethylphosphino)phenyl]-N'-phenylurea and N-[2-(ethyl P-ethylphosphino)phenyl]-N'-methylurea are prepared by reacting ethyl P-ethyl-2-aminophenylphosphinate with, respectively, N-phenylisocyanate and N-methylisocyanate.

Each of the above three ureas is cyclized, following the procedure of Example 1, to give
1-ethyl-2-isopropyl-4H-1,2,3,4-tetrahydro-2,4,1-benzodiazaphosphorin-1,3-dione;
1-ethyl-2-phenyl-4H-1,2,3,4-tetrahydro-2,4,1-benzodiazaphosphorin-1,3-dione; and
1-ethyl-2-methyl-4H-1,2,3,4-tetrahydro-2,4,1-benzodiazaphosphorin-1,3-dione.

EXAMPLE 10

A mixture of 1-methyl-2-isopropyl-4H-1,2,3,4-tetrahydro-2,4,1-benzodiazaphosphorin-1,3-dione (10.0 mmol), saturated sodium bicarbonate (40 ml) and methyl sulfate (150.0 mmol) is stirred at RT for 3 hours. The reaction mixture is extracted with methylene chloride, and the extract is washed, dried and evaporated to give 1,4-dimethyl-2-isopropyl-4H-1,2,3,4-tetrahydro-2,4,1-benzodiazaphosphorin-1,3-dione.

EXAMPLE 11

A mixture of 1-methyl-2-isopropyl-4H-1,2,3,4-tetrahydro-2,4,1-benzodiazaphosphorin-1,3-dione (10 mmol), para-formaldehyde (360 mg) and sulfinyl chloride (3 ml) in 20 ml of toluene is heated to 100° until the solution is clear. The reaction mixture is then concentrated to dryness to give 1-methyl-2-isopropyl-4-chloromethyl-4H-1,2,3,4-tetrahydro-2,4,1-benzodiazaphosphorin-1,3-dione.

EXAMPLE 12

A mixture of 1-methyl-2-isopropyl-4-chloromethyl-4H-1,2,3,4-tetrahydro-2,4,1-benzodiazaphosphorin-1,3-dione (10 mmol) and methanol (10 ml) is heated under reflux for 1 hour. Hydrogen chloride is flushed from the refluxing mixture by a stream of nitrogen gas during the reaction. The reaction mixture is then evaporated to dryness to give 1-methyl-2-isopropyl-4-methoxymethyl-4H-1,2,3,4-tetrahydro-2,4,1-benzodiazaphosphorin-1,3-dione.

EXAMPLE 13

A slurry of 1-methyl-2-isopropyl-4H-1,2,3,4-tetrahydro-2,4,1-benzodiazaphosphorin-1,3-dione (10.0 mmol) and sodium hydride (50% oil, 12.0 mmol) in 10 ml of anhydrous tetrahydrofuran is stirred at RT for 1 hour, after which chloroacetonitrile (15.0 mmol) is added. The reaction mixture is stirred at room temperature overnight. It is then poured into water and extracted with methylene chloride (3X). The combined extracts are washed, dried, evaporated and purified by chromatography (silica gel, 20% ethyl acetate/hexane) to yield 1-methyl-2-isopropyl-4-cyanomethyl-4H-1,2,3,4-tetrahydro-2,4,1-benzodiazaphos-phorin-1,3-dione.

EXAMPLE 14

Following the procedure of Example 5, 7-phenylthio-1-methyl-2-isopropyl-4H-1,2,3,4-tetrahydro-2,4,1-benzodiazaphosphorin-1,3-dione in methanol is reacted with sodium periodate to give 7-phenylsulfinyl-1-methyl-2-isopropyl-4H-1,2,3,4-tetrahydro-2,4,1-benzodiazaphosphorin-1,3-dione.

EXAMPLE 15

Following the procedure of Example 6, 7-phenylthio-1-methyl-2-isopropyl-4H-1,2,3,4-tetrahydro-2,4,1-benzodiazaphosphorin-1,3-dione in acetic acid is reacted with 30% hydrogen peroxide to give 7-phenylsulfonyl-1-methyl-2-isopropyl-4H-1,2,3,4-tetrahydro-2,4,1-benzodiazaphosphorin-1,3-dione.

EXAMPLE 16

To a solution of potassium hydroxide pellets (10.0 mmol) dissolved in ethanol (50 ml) is added ethyl P-methyl-2-nitro-5-chlorophenylphosphinate (20.0 mmol). The mixture is boiled for 48 hours and is then concentrated to a slurry. The residue is diluted with water, acidified with 10% HCl and extracted with ethyl acetate (2X). The combined extracts are washed with brine, dried and evaporated to yield ethyl P-methyl-2-nitro-5-ethoxyphenylphosphinate.

Following the procedure of Example 1, ethyl P-methyl-2-nitro-5-ethoxyphenylphosphinate is hydrogenated to the aminophenylphosphinate, which is then reacted with N-isopropylisocyanate. The resulting N-[2-(ethyl P-methylphosphino)-4-ethoxyphenyl]-N'-isopropylurea is cyclized to give 7-ethoxy-1-methyl-2-isopropyl-4H-1,2,3,4-tetrahydro-2,4,1-benzodiazaphosphorin-1,3-dione.

EXAMPLE 17

A mixture of ethyl P-methyl-2-nitro-5-chlorophenylphosphinate (20.0 mmol), 4-chlorophenol (30.0 mmol) and potassium carbonate (30.0 mmol) in dimethylformamide (20 ml) is heated to 120° for 8 hours. The reaction mixture is filtered, and the filtrate is poured into water, acidified with dilute HCl and extracted with methylene chloride. The extract is washed, dried and evaporated to dryness to give, after purification by chromatography (silica gel, 20% ethyl acetate/hexane), ethyl P-methyl-2-nitro-5-(4-chlorophenoxy)phenylphosphinate.

Following the procedures of Example 1, ethyl P-methyl-2-nitro-5-(4-chlorophenoxy)phenylphosphinate is hydrogenated to the corresponding aminophenylphosphinate, which is reacted with N-isopropylisocyanate. The resulting N-[2-(ethyl P-methylphosphino)-4-(4-chlorophenoxy)phenyl]-N'-isopropyl-urea is cyclized to give 7-(4-chlorophenoxy)-1-methyl-2-isopropyl-4H-1,2,3,4-tetrahydro-2,4,1-benzodiazaphosphorin-1,3-dione.

In the same manner as above, each of 7-phenoxy-1-methyl-2-isopropyl-4H-1,2,3,4-tetrahydro-2,4,1-benzodiazaphosphorin-1,3-dione and 7-(2,4-dichlorophenoxy)-1-methyl-2-isopropyl-4H-1,2,3,4-tetrahydro-2,4,1-benzodiazaphosphorin-1,3-dione is prepared by the reaction of ethyl P-methyl-2-nitro-5-chlorophenylphosphinate with, respectively, phenol and 2,4-dichlorophenol.

EXAMPLE 18

Following the procedure of Example 17, ethyl P-methyl-2-nitro-5-chlorophenylphosphinate and 2-pyridyl alcohol are reacted together to give ethyl P-methyl-2-nitro-5-(2-pyridyloxy)phenoxyphosphinate.

Following Example 1 procedures, this nitrophenylphosphinate is hydrogenated to the corresponding aminophenylphosphinate, which is reacted with N-isopropylisocyanate. The resulting N-[2-(ethyl P-methylphosphino)-4-(2-pyridyloxy)phenyl]-N'-isopropylurea is cyclized to yield 7-(2-pyridyloxy)-1-methyl-2-isopropyl-4H-1,2,3,4-tetrahydro-2,4,1-benzodiazaphosphorin-1,3-dione.

In like manner, ethyl P-methyl-2-nitro-5-chlorophenylphosphinate is reacted with each of 5-chloro-2-pyridyl alcohol, 3,5-dichloro-2-pyridyl alcohol and 3-chloro-5-trifluoromethyl-2-pyridylalcohol to give, respectively, ethyl P-methyl-2-nitro-5-(5-chloro-2-pyridyloxy)-phenylphosphinate, ethyl P-methyl-2-nitro-5-(3,5-dichloro-2-pyridyloxy)-phenylphosphinate, and ethyl P-methyl-2-nitro-5-(3-chloro-5-trifluoromethyl-2-pyridyloxy)phenylphosphinate.

Each of the above nitrophenylphosphinates is hydrogenated to the corresponding aminophenylphosphinate, which is reacted with N-isopropylisocyanate to give, respectively, N-[2-(ethyl P-methylphosphino)-4-(5-chloro-2-pyridyloxy)phenyl]-N'-isopropylurea, N-[2-(ethyl P-methylphosphino)-4-(3,5-dichloro-2-pyridyloxy)phenyl]-N'-isopropylurea, and N-[2-(ethyl P-methylphosphino)-4-(3-chloro-5-trifluoromethyl-2-pyridyloxy)phenyl]-N'-isopropylurea.

Each of the above ureas is cyclized to yield, respectively, 7-(5-chloro-2-pyridyloxy)-1-methyl-2-isopropyl-4H-1,2,3,4-tetrahydro-2,4,1-benzodiazaphosphorin-1,3-dione;

7-(3,5-dichloro-2-pyridyloxy)-1-methyl-2-isopropyl-4H-1,2,3,4-tetrahydro-2,4,1-benzodiazaphosphorin-1,3-dione; and 7-(3-chloro-5-trifluoromethyl-2-pyridyloxy)-1-methyl-2-isopropyl-4H-1,2,3,4-tetrahydro-2,4,1-benzodiazaphosphorin-1,3-dione.

EXAMPLE 19

Following the procedure of Example 8, ethyl P-methyl-2-nitro-5-chlorophenylphosphinate is reacted with each of 2-pyridylthiol and 5-chloro-2-pyridylthiol to give, respectively, methyl P-methyl-2-nitro-5-(2-pyridylthio)-phenylphosphinate and methyl P-methyl-2-nitro-5-(5-chloro-2-pyridylthio)phenylphosphinate, each of which is hydrogenated to, respectively, methyl P-methyl-2-amino-5-(2-pyridylthio)phenylphosphinate and methyl P-methyl-2-amino-5-(5-chloro-2-pyridylthio)phenylphosphinate. Each of these two amino-phenylphosphinates is reacted with N-isopropylisocyanate to give, respectively, N-[2-(methyl P-methylphosphino)-4-(2-pyridylthio)phenyl]-N'-isopropylurea and N-[2-(methyl P-methylphosphino)-4-(5-chloro-2-pyridylthio)phenyl]-N'-isopropylurea, each of which is then cyclized to give, respectively, 7-(2-pyridylthio)-1-methyl-2-isopropyl-4H-1,2,3,4-tetrahydro-2,4,1-benzodiazaphosphorin-1,3-dione and 7-(5-chloro-2-pyridylthio)-1-methyl-2-isopropyl-4H-1,2,3,4-tetrahydro-2,4,1-benzodiazaphosphorin-1,3,-dione.

EXAMPLE 20

Following the procedure of Example 5, 7-(2-pyridylthio)-1-methyl-2-isopropyl-4H-1,2,3,4-tetrahydro-2,4,1-benzodiazaphosphorin-1,3-dione is reacted with sodium periodate to yield 7-(2-pyridylsulfinyl)-1-methyl-2-isopropyl-4H-1,2,3,4-tetrahydro-2,4,1-benzodiazaphosphorin-1,3-dione.

EXAMPLE 21

Following the procedure of Example 6, 7-(2-pyridylthio)-1-methyl-2-isopropyl-4H-1,2,3,4-tetrahydro-2,4,1-benzodiazaphosphorin-1,3-dione, in acetic acid, and hydrogen peroxide are reacted together to yield 7-(2-pyridylsulfonyl)-1-methyl-2-isopropyl-4H-1,2,3,4-tetrahydro-2,4,1-benzodiazaphosphorin-1,3-dione.

EXAMPLE 22

A mixture of 2-chloro-3-nitropyridine (10.0 mmol) and anhydrous nickel chloride (0.10 mmol) is stirred under a nitrogen atmosphere at 160°. While the temperature is maintained at 160°–170°, diethyl methylphosphonite (20.0 mmol) is added dropwise to the mixture. The reaction mixture is heated at 165°–175° for an hour and is then allowed to cool to RT. It is then poured onto ice water and extracted with chloroform. The chloroform extracts are washed with water, dried over magnesium sulfate and concentrated in vacuo to yield 2-(ethyl P-methylphosphino)-3-nitropyridine.

Following the procedure of Example 1, 2-(ethyl P-methylphosphino)-3-nitropyridine is hydrogenated to the corresponding aminopyridine, which is then reacted with N-isopropylisocyanate. The resulting 2-(ethyl P-methylphosphino)-3-(N'-isopropylureido)pyridine is cyclized to yield 1-methyl-2-isopropyl-4H-1,2,3,4-tetrahydro-2,4,1-(8-pyrido)diazaphosphorin-1,3-dione.

EXAMPLE 23

Following the procedure of Example 22, 2-(ethyl P-methylphosphino)-3-aminopyridine is reacted with each of N-phenylisocyanate, N-methylisocyanate, isocyanate and N-(4-chlorophenyl)isocyanate to yield, respectively,
2-(ethyl P-methylphosphino)-3-(N'-phenylureido)pyridine,
2-(ethyl P-methylphosphino)-3-(N'-methylureido)pyridine,
2-(ethyl P-methylphosphino)-3-ureidopyridine, and
2-(ethyl P-methylphosphino)-3-[N'-(4-chlorophenyl)ureido]pyridine.

Each of the above ureidopyridines is then cyclized to yield, respectively,
1-methyl-2-phenyl-4H-1,2,3,4-tetrahydro-2,4,1-(8-pyrido)diazaphosphorin-1,3-dione;
1,2-dimethyl-4H-1,2,3,4-tetrahydro-2,4,1-(8-pyrido)diazaphosphorin-1,3-dione;
1-methyl-4H-1,2,3,4-tetrahydro-2,4,1-(8-pyrido)diazaphosphorin-1,3-dione; and
1-methyl-2-(4-chlorophenyl)-4H-1,2,3,4-tetrahydro-2,4,1-(8-pyrido)diazaphosphorin-1,3-dione.

EXAMPLE 24

Oxalylchloride (30.0 mmol) and N,N-dimethylformamide (1 drop) triethylamine (0.2 ml) are added to a solution of ethyl P-methyl-2-nitrophenylphosphinate (10.0 mmol) in methylene chloride (20 ml), and the mixture is stirred at RT for 3 hours. Excess oxalyl chloride is removed by evaporation, and isopropylamine (20.0 mmol) in methylene chloride (10 ml) is added to the residue. The mixture is stirred at RT for several hours, after which it is filtered, washed and evaporated to dryness to give N-isopropyl-P-methyl-2-nitrophenylphosphinamide.

A solution of N-isopropyl-P-methyl-2-nitrophenylphosphinamide (10 mmol) in ethanol (40 ml) containing 10% palladium on carbon (200 mg) is hydrogenated at atmospheric pressure. After cessation of hydrogen uptake, the mixture is filtered and evaporated to dryness to give N-isopropyl-P-methyl-(2-aminophenyl)phosphinamide.

A solution of N-isopropyl-P-methyl-(2-aminophenyl)-phosphinamide (20.0 mmol) in chlorobenzene (40.0 ml) containing phosgene (80.0 mmol) is heated under reflux for 6 hours. Excess phosgene and chlorobenzene are removed by distillation to yield 1-methyl-2-isopropyl-4H-1,2,3,4-tetrahydro-2,4,1-benzodiazaphosphorin-1,3-dione.

EXAMPLE 25

Following the procedure of Example 24, N-isopropyl-P-methyl-(2-aminophenyl)phosphinamide is prepared and is then cyclized by reacting with thiophosgene in chlorobenzene to yield 1-methyl-2-isopropyl-3-thio-4H-1,2,3,4-tetrahydro-2,4,1-benzodiazaphosphorin-1,3-dione.

EXAMPLE 26

Following the procedure of Example 24, ethyl P-methyl-2-nitrophenylphosphinate is treated with phosgene and is then reacted with each of phenylamine, methylamine & 4-chlorophenylamine to give, respectively,
N-phenyl-P-methyl-(2-nitrophenyl)phosphinamide,
N-methyl-P-methyl-(2-nitrophenyl)phosphinamide, and
N-(4-chlorophenyl)-P-methyl-(2-nitrophenyl)phosphinamide.

Each of the above nitrophenylphosphinamides is hydrogenated to the corresponding aminophenylphosphinamide, which is then cyclized by reacting with thiophosgene in chlorobenzene to yield, respectively,
1-methyl-2-phenyl-3-thio-4H-1,2,3,4-tetrahydro-2,4,1-benzodiazaphosphorin-1,3-dione;
1,2-dimethyl-3-thio-4H-1,2,3,4-tetrahydro-2,4,1-benzodiazaphosphorin-1,3-dione; and
1-methyl-2-(4-chlorophenyl)-3-thio-4H-1,2,3,4-tetrahydro-2,4,1-benzodiazaphosphorin-1,3-dione.

EXAMPLE 27

Following the procedure of Example 24, isopropylamine is reacted with each of ethyl P-methyl-2-nitro-5-chlorophenylphosphinate, ethyl P-methyl-2-nitro-5-methoxyphenylphosphinate, ethyl P-methyl-2-nitro-5-ethylphenylphosphinate, ethyl P-methyl-2-nitro-5-trifluoromethylphenylphosphinate and ethyl P-methyl-2-nitro-5-ethoxyphenylphosphinate to give, respectively,
N-isopropyl-P-methyl-(2-nitro-5-chlorophenyl)phosphinamide,
N-isopropyl-P-methyl-(2-nitro-5-methoxyphenyl)phosphinamide,
N-isopropyl-P-methyl-(2-nitro-5-ethylphenyl)phosphinamide,
N-isopropyl-P-methyl-(2-nitro-5-trifluoromethylphenyl)phosphinamide, and
N-isopropyl-P-methyl-(2-nitro-5-ethoxyphenyl)-phosphinamide.

Each of the above nitrophenylphosphinamides is hydrogenated to the corresponding aminophenylphosphinamide, which is then cyclized by reacting with thiophosgene to yield, respectively, 1-methyl-2-isopropyl-3-thio-7-chloro-4H-1,2,3,4-tetrahydro-2,4,1-benzodiazaphosphorin-1,3-dione;

1-methyl-2-isopropyl-3-thio-7-methoxy-4H-1,2,3,4-tetrahydro-2,4,1-benzodiazaphosphorin-1,3-dione;

1-methyl-2-isopropyl-3-thio-7-ethyl-4H-1,2,3,4-tetrahydro-2,4,1-benzodiazaphosphorin-1,3-dione;

1-methyl-2-isopropyl-3-thio-7-trifluoromethyl-4H-1,2,3,4-tetrahydro-2,4,1-benzodiazaphosphorin-1,3-dione; and 1-methyl-2-isopropyl-3-thio-7-ethoxy-4H-1,2,3,4-tetrahydro-2,4,1-benzodiazaphosphorin-1,3-dione.

EXAMPLE 28

Methyl P-methyl-2-nitro-5-ethylthiophenylphosphinate, prepared as in Example 4, is reacted with isopropylamine to give N-isopropyl-P-methyl-(2-nitro-5-ethylthiophenyl)-phosphinamide, following the procedure of Example 24. This is then hydrogenated to the corresponding aminophenylphosphinamide, which is then cyclized by reacting with thiophosgene, following Example 24 procedures, to yield 1-methyl-2-isopropyl-3-thio-7-ethylthio-4H-1,2,3,4-tetrahydro-2,4,1-benzodiazaphosphorin-1,3-dione.

In like manner, 1-methyl-2-isopropyl-3-thio-7-phenylthio-4H-1,2,3,4-tetrahydro-2,4,1-benzodiazaphosphorin-1,3-dione is prepared by the reaction of methyl P-methyl-2-nitro-5-phenylthiophenylphosphinate and isopropylamine, followed by hydrogenation & cyclization with thiophosgene. Methyl P-methyl-2-nitro-5-phenylthiophenylphosphinate can be prepared as described in Example 8.

EXAMPLE 29

Following the procedure of Example 5, each of 1-methyl-2-isopropyl-3-thio-7-ethylthio-4H-1,2,3,4-tetrahydro-2,4,1-benzodiazaphosphorin-1,3-dione and 1-methyl-2-isopropyl-3-thio-7-phenylthio-4H-1,2,3,4-tetrahydro-2,4,1-benzodiazaphosphorin-1,3-dione in methanol is reacted with sodium periodate to yield, respectively, 1-methyl-2-isopropyl-3-thio-7-ethylsulfinyl-4H-1,2,3,4-tetrahydro-2,4,1-benzodiazaphosphorin-1,3-dione and 1-methyl-2-isopropyl-3-thio-7-phenylsulfinyl-4H-1,2,3,4-tetrahydro-2,4,1-benzodiazaphosphorin-1,3-dione.

EXAMPLE 30

Following the procedure of Example 6, each of 1-methyl-2-isopropyl-3-thio-7-ethylthio-4H-1,2,3,4-tetrahydro-2,4,1-benzodiazaphosphorin-1,3-dione and 1-methyl-2-isopropyl-3-thio-7-phenylthio-4H-1,2,3,4-tetrahydro-2,4,1-benzodiazaphosphorin-1,3-dione in acetic acid is reacted with hydrogen peroxide to yield, respectively, 1-methyl-2-isopropyl-3-thio-7-ethylsulfonyl-4H-1,2,3,4-tetrahydro-2,4,1-benzodiazaphosphorin-1,3-dione and 1-methyl-2-isopropyl-3-thio-7-phenylsulfonyl-4H-1,2,3,4-tetrahydro-2,4,1-benzodiazaphosphorin-1,3-dione.

EXAMPLE 31

Following the procedure of Example 24, each of ethyl P-methyl-2-nitro-5-phenoxyphenylphosphinate and ethyl P-methyl-2-nitro-5-(4-chlorophenoxy)phenylphosphinate (prepared as in Example 17) is reacted with isopropylamine to give, respectively, N-isopropyl-P-methyl-(2-nitro-5-phenoxyphenyl)-phosphinamide and N-isopropyl-P-methyl-[2-nitro-5-(4-chlorophenoxy)]-phenylphosphinamide. Each of these nitrophenylphosphinamides is hydrogenated to the corresponding aminophenylphosphinamide, which is then cyclized by reaction with thiophosgene to yield, respectively, 1-methyl-2-isopropyl-3-thio-7-phenoxy-4H-1,2,3,4-tetrahydro-2,4,1-benzodiazaphosphorin-1,3-dione and 1-methyl-2-isopropyl-3-thio-7-(4-chlorophenoxy)-4H-1,2,3,4-tetrahydro-2,4,1-benzodiazaphosphorin-1,3-dione.

EXAMPLE 32

Oxalyl chloride (30.0 mmol) and N,N-dimethylformamide (1 drop) are added to a solution of ethyl P-methyl-2-nitrophenylphosphinate (10.0 mmol) in methylene chloride (20 ml), and the mixture is stirred at RT for 3 hours. Excess oxalyl chloride is removed by evaporation, and ethyl N-isopropylcarbamate (20.0 mmol) in methylene chloride (10 ml) is added to the residue. The mixture is stirred at RT for several hours, after which it is filtered, washed and evaporated to give N-isopropyl-N-carboethoxy-P-methyl-(2-nitrophenyl)phosphinamide.

Following the procedure of Example 24, the above carbamate is hydrogenated to N-isopropyl-N-carboethoxy-P-methyl-(2-aminophenyl)phosphinamide, followed by cyclization following one of the procedures of Example 1 or Example 24 to yield 1-methyl-2-isopropyl-4H-1,2,3,4-tetrahydro-2,4,1-benzodiazaphos-phorin-1,3-dione.

In like manner, N-isopropyl-N-carboethoxy-P-methyl-(2-nitro-5-chlorophenyl)phosphinamide, N-isopropyl-N-carboethoxy-P-methyl-(2-nitro-5-ethoxyphenyl)-phosphinamide, and N-isopropyl-N-carboethoxy-P-methyl-(2-nitro-5-ethylthio)phosphinamide are prepared by reacting ethyl N-isopropylcarbamate with each of ethyl P-methyl-2-nitro-5-chlorophenylphosphinate, ethyl P-methyl-2-nitro-5-ethoxyphenylphosphinate and ethyl P-methyl-2-nitro-5-ethylthiophenylphosphinate. Each of the above three phosphinamides is hydrogenated and then cyclized to yield, respectively, 1-methyl-2-isopropyl-7-chloro-4H-1,2,3,4-tetrahydro-2,4,1-benzodiazaphosphorin-1,3-dione;

1-methyl-2-isopropyl-7-ethoxy-4H-1,2,3,4-tetrahydro-2,4,1-benzodiazaphosphorin-1,3-dione; and 1-methyl-2-isopropyl-7-ethylthio-4H-1,2,3,4-tetrahydro-2,4,1-benzodiazaphosphorin-1,3-dione.

EXAMPLE 33

To 4-chloro-1,2-dinitrobenzene (13.2 g, 65.0 mmol) dissolved in acetonitrile (150 ml) is added, dropwise, diethyl methylphosphonite (16.0 g, 117.6 mmol). The mixture is stirred at RT for 20 hours, after which it is concentrated. The crude product is purified by column chromatography (developing with 50% ethyl acetate/hexane) to yield ethyl P-methyl-2-nitro-5-chlorophenylphosphinate.

Ethyl P-methyl-2-nitro-5-chlorophenylphosphinate (1.7 g, 7.5 mmol) dissolved in methanol (25 ml) is added to 200 mg of 5% palladium on carbon. The mixture is hydrogenated at 32 psi for 1 hour. The catalyst is then filtered off and the filtrate is evaporated to dryness to give ethyl P-methyl-2-amino-5-chlorophenylphosphinate.

EXAMPLE 34

A mixture of ethyl P-methyl-2-aminophenylphosphinate (1.0 g, 5.0 mmol) and N-isopropylisocyanate (1.5 ml, 15.0 mmol) in tetrahydrofuran (40 ml) is heated under reflux for 5 hours. The solvent is evaporated off under vacuum to give N-[2-ethyl P-methylphosphino)-phenyl]-N'-isopropylurea.

A mixture of N-[2-(ethyl P-methylphosphino)-phenyl]-N'-isopropylurea (1.3 g, 4.6 mmol) and thionyl chloride (2 ml) in chloroform (10 ml) is heated under reflux for 4 hours. Excess thionyl chloride and chloroform are evaporated off under vacuum to give N-[2-(P-methylphosphinochloridato)phenyl]-N'-isopropylurea.

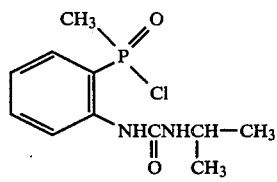

To the above N-[2-(P-methylphosphinochloridato)-phenyl]-N'-isopropylurea, redissolved in chloroform, is added triethylamine (3.5 ml). The mixture is stirred at RT overnight. It is then washed with water (2X) and concentrated to dryness. The crude product is purified by prep. TLC (silica gel, developing with 5% methanol/methylene chloride) to give 1-methyl-2-isopropyl-4H-1,2,3,4-tetrahydro-2,4,1-benzodiazaphosphorin-1,3-dione.

What is claimed is:

1. A compound of the following formula (III):

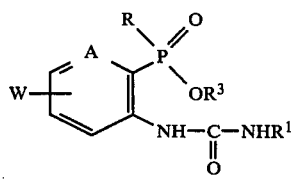

(III)

wherein,

A is CH or N;

R is lower alkyl or phenyl;

$R^1$ is hydrogen, lower alkyl, lower cycloalkyl, or phenyl, unsubstituted or substituted at one, two or three of the ring carbon atoms by radicals selected from halogen, lower alkyl, lower alkoxy, lower haloalkyl, or lower alkylthio;

$R^3$ is lower alkyl; and

W is hydrogen, lower alkyl, lower haloalkyl, lower alkoxy, lower alkylthio, lower alkylsulfinyl, lower alkylsulfonyl, halogen or the group

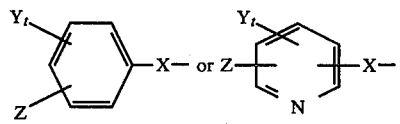

where X is oxygen, sulfur, sulfinyl or sulfonyl; t is zero, one or two; and Y and Z is independently selected from hydrogen, lower alkyl, lower alkoxy, lower haloalkyl, lower haloalkoxy or halogen.

2. A compound according to claim 1 wherein R is methyl or ethyl; $R^1$ is methyl, ethyl, isopropyl, cyclopropyl or phenyl; $R^3$ is methyl or ethyl; and W is hydrogen, methyl, ethyl, isopropyl, trifluoromethyl, methoxy, ethoxy, methylthio, ethylthio, methylsulfinyl, ethylsulfinyl, methylsulfonyl, ethylsulfonyl, chloro, bromo or the group:

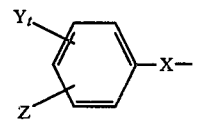

where t is zero or one, Y is hydrogen or chloro and Z is hydrogen, chloro or trifluoromethyl.

3. A compound according to claim 2 wherein A is CH.

4. A compound according to claim 3 wherein $R^1$ is isopropyl and W is hydrogen, methyl, trifluoromethyl or chloro and is in the 4 position.

5. A compound according to claim 2 wherein A is N.

* * * * *